United States Patent
Chester et al.

(10) Patent No.: US 7,056,282 B2
(45) Date of Patent: Jun. 6, 2006

(54) COOLANT CONTROL FOR RAPID INDUCTION OF MILD HYPOTHERMIA

(75) Inventors: Steven M. Chester, Kirkland, WA (US); Martin S. Abbenhouse, Kirkland, WA (US); Stephen W. Radons, Snohomish, WA (US)

(73) Assignee: Medtronic Emergency Response Systems, Inc., Redmond, WA (US)

( * ) Notice: Subject to any disclaimer, the term of this patent is extended or adjusted under 35 U.S.C. 154(b) by 88 days.

(21) Appl. No.: 10/632,122

(22) Filed: Jul. 31, 2003

(65) Prior Publication Data

US 2005/0101911 A1    May 12, 2005

Related U.S. Application Data

(60) Provisional application No. 60/436,433, filed on Dec. 23, 2002.

(51) Int. Cl.
*A61F 7/00* (2006.01)

(52) U.S. Cl. .................. 600/107; 600/104; 600/114

(58) Field of Classification Search ............... 607/96, 607/104, 107–112, 114; 62/50.2, 87, 222–223, 62/259.3; 602/13–14; 601/148, 151
See application file for complete search history.

(56) References Cited

U.S. PATENT DOCUMENTS

| | | | |
|---|---|---|---|
| 3,504,674 A | 4/1970 | Swenson et al. | |
| 3,587,544 A | 6/1971 | Smirnov et al. | |
| 3,648,765 A | 3/1972 | Starr | |
| 3,811,777 A | 5/1974 | Chance | |
| 3,830,222 A | 8/1974 | Chance | |
| 3,871,381 A | 3/1975 | Roslonski | |
| 3,963,351 A | 6/1976 | Chance et al. | |
| 4,023,905 A | 5/1977 | Chance | |
| 4,118,946 A | 10/1978 | Tubin | |
| 4,138,743 A | 2/1979 | Elkins et al. | |
| 4,162,405 A | 7/1979 | Chance et al. | |
| 4,172,495 A | 10/1979 | Zebuhr et al. | |
| 4,191,028 A | 3/1980 | Audet et al. | |
| 4,292,973 A * | 10/1981 | Yamauchi et al. | 607/107 |
| 4,378,797 A | 4/1983 | Osterholm | |
| 4,380,240 A | 4/1983 | Jobsis et al. | |
| 4,382,446 A | 5/1983 | Truelock et al. | |
| 4,416,285 A | 11/1983 | Shaw et al. | |

(Continued)

FOREIGN PATENT DOCUMENTS

GB    764993    1/1957

(Continued)

OTHER PUBLICATIONS

US 6,645,236, 11/2003, Lachenbruch et al. (withdrawn)

*Primary Examiner*—John P. Leubecker
(74) *Attorney, Agent, or Firm*—Shumaker & Sieffert, P.A.

(57) ABSTRACT

The invention is directed to techniques and apparatus for controlling the temperature of a coolant delivered to a patient in a hypothermic therapy system, including a hypothermic therapy system that can be applied to a patient outside or inside a hospital setting. In general, the coolant is in a pressurized form at ambient temperature, and is expanded proximate to the patient to cause the coolant to cool. Cooling garments placed in contact with the body of the patient circulate the cooled coolant proximate to the patient to cool the patient. A controller controls the temperature of the coolant by mixing the coolant with ambient air, for example, to reduce the risk of harm the patient.

31 Claims, 4 Drawing Sheets

U.S. PATENT DOCUMENTS

| | | |
|---|---|---|
| 4,425,916 A | 1/1984 | Bowen |
| 4,441,502 A | 4/1984 | Chance |
| 4,452,250 A | 6/1984 | Chance et al. |
| 4,510,938 A | 4/1985 | Jobsis et al. |
| 4,552,149 A | 11/1985 | Tatsuki |
| 4,570,638 A | 2/1986 | Stoddart et al. |
| 4,638,436 A | 1/1987 | Badger et al. |
| 4,725,147 A | 2/1988 | Stoddart |
| 4,750,493 A | 6/1988 | Brader |
| 4,753,242 A | 6/1988 | Saggers |
| 4,765,338 A | 8/1988 | Turner et al. |
| 4,768,516 A | 9/1988 | Stoddart et al. |
| 4,817,621 A | 4/1989 | Aaslid |
| 4,817,623 A | 4/1989 | Stoddart et al. |
| 4,865,038 A | 9/1989 | Rich et al. |
| 4,869,250 A | 9/1989 | Bitterly |
| 4,904,237 A | 2/1990 | Janese |
| 4,920,963 A | 5/1990 | Brader |
| 4,964,408 A | 10/1990 | Hink et al. |
| 4,972,331 A | 11/1990 | Chance |
| 4,981,136 A | 1/1991 | Chance |
| 4,987,896 A | 1/1991 | Nakamatsu |
| 5,062,428 A | 11/1991 | Chance |
| 5,080,098 A | 1/1992 | Willett et al. |
| 5,081,991 A | 1/1992 | Chance |
| 5,090,415 A | 2/1992 | Yamashita et al. |
| 5,094,240 A | 3/1992 | Muz |
| 5,110,721 A | 5/1992 | Anaise et al. |
| 5,119,815 A | 6/1992 | Chance |
| 5,122,974 A | 6/1992 | Chance |
| 5,139,025 A | 8/1992 | Lewis et al. |
| 5,140,989 A | 8/1992 | Lewis et al. |
| 5,149,321 A | 9/1992 | Klatz et al. |
| 5,163,425 A | 11/1992 | Nambu et al. |
| 5,167,230 A | 12/1992 | Chance |
| 5,187,672 A | 2/1993 | Chance et al. |
| 5,188,108 A | 2/1993 | Secker |
| 5,217,013 A | 6/1993 | Lewis et al. |
| 5,234,405 A | 8/1993 | Klatz et al. |
| 5,261,243 A * | 11/1993 | Dunsmore ................ 62/52.1 |
| 5,261,399 A | 11/1993 | Klatz et al. |
| 5,269,758 A | 12/1993 | Taheri |
| 5,287,705 A * | 2/1994 | Roehrich et al. ............ 62/50.3 |
| 5,349,961 A | 9/1994 | Stoddart et al. |
| 5,350,417 A | 9/1994 | Augustine |
| 5,353,799 A | 10/1994 | Chance |
| 5,365,607 A | 11/1994 | Benevento, Jr. et al. |
| 5,383,918 A | 1/1995 | Panetta |
| 5,386,827 A | 2/1995 | Chance et al. |
| 5,395,314 A | 3/1995 | Klatz et al. |
| 5,402,778 A | 4/1995 | Chance |
| 5,408,093 A | 4/1995 | Ito et al. |
| 5,409,005 A | 4/1995 | Bissonnette et al. |
| 5,449,379 A | 9/1995 | Hadtke |
| 5,465,714 A | 11/1995 | Scheuing |
| 5,477,853 A | 12/1995 | Farkas et al. |
| 5,482,034 A | 1/1996 | Lewis et al. |
| 5,486,204 A | 1/1996 | Clifton |
| 5,531,776 A | 7/1996 | Ward et al. |
| 5,553,614 A | 9/1996 | Chance |
| 5,555,885 A | 9/1996 | Chance |
| 5,564,417 A | 10/1996 | Chance |
| 5,584,296 A | 12/1996 | Cui et al. |
| 5,584,804 A | 12/1996 | Klatz et al. |
| 5,596,987 A | 1/1997 | Chance |
| 5,603,728 A | 2/1997 | Pachys |
| 5,658,324 A | 8/1997 | Bailey, Sr. et al. |
| 5,664,574 A | 9/1997 | Chance |
| 5,673,701 A | 10/1997 | Chance |
| 5,683,438 A | 11/1997 | Grahn |
| 5,697,367 A | 12/1997 | Lewis et al. |
| 5,700,828 A | 12/1997 | Federowicz et al. |
| 5,713,941 A | 2/1998 | Robins et al. |
| 5,716,386 A | 2/1998 | Ward et al. |
| 5,730,730 A | 3/1998 | Darling, Jr. |
| 5,755,756 A | 5/1998 | Freedman, Jr. et al. |
| 5,779,631 A | 7/1998 | Chance |
| 5,782,755 A | 7/1998 | Chance et al. |
| 5,792,051 A | 8/1998 | Chance |
| 5,795,292 A | 8/1998 | Lewis et al. |
| 5,802,865 A | 9/1998 | Strauss |
| 5,807,263 A | 9/1998 | Chance |
| 5,820,558 A | 10/1998 | Chance |
| 5,827,222 A | 10/1998 | Klatz et al. |
| 5,837,003 A | 11/1998 | Ginsburg |
| 5,853,370 A | 12/1998 | Chance et al. |
| 5,860,292 A | 1/1999 | Augustine et al. |
| 5,871,526 A | 2/1999 | Gibbs et al. |
| 5,873,821 A | 2/1999 | Chance et al. |
| 5,899,865 A | 5/1999 | Chance |
| 5,902,235 A | 5/1999 | Lewis et al. |
| 5,913,885 A | 6/1999 | Klatz et al. |
| 5,916,242 A | 6/1999 | Schwartz |
| 5,917,190 A | 6/1999 | Yodh et al. |
| 5,954,053 A | 9/1999 | Chance et al. |
| 5,957,963 A | 9/1999 | Dobak, III |
| 5,964,092 A | 10/1999 | Tozuka et al. |
| 5,987,351 A | 11/1999 | Chance |
| 6,010,528 A | 1/2000 | Augustine et al. |
| 6,012,179 A | 1/2000 | Garrett et al. |
| 6,030,412 A | 2/2000 | Klatz et al. |
| 6,044,648 A | 4/2000 | Rode |
| 6,058,324 A | 5/2000 | Chance |
| 6,090,132 A | 7/2000 | Fox |
| 6,110,168 A | 8/2000 | Ginsburg |
| 6,119,474 A | 9/2000 | Augustine et al. |
| 6,126,680 A | 10/2000 | Wass |
| 6,149,624 A | 11/2000 | McShane |
| 6,149,670 A | 11/2000 | Worthen et al. |
| 6,149,673 A | 11/2000 | Ginsburg |
| 6,149,677 A | 11/2000 | Dobak, III |
| 6,156,007 A | 12/2000 | Ash |
| 6,156,057 A | 12/2000 | Fox |
| 6,183,501 B1 | 2/2001 | Latham |
| 6,188,930 B1 | 2/2001 | Carson |
| 6,209,144 B1 | 4/2001 | Carter |
| 6,248,126 B1 | 6/2001 | Lesser et al. |
| 6,277,143 B1 | 8/2001 | Klatz et al. |
| 6,283,123 B1 | 9/2001 | Van Meter et al. |
| 6,303,156 B1 | 10/2001 | Ferrigno |
| 6,325,818 B1 | 12/2001 | Werneth |
| 6,354,099 B1 | 3/2002 | Bieberich |
| 6,375,673 B1 | 4/2002 | Clifton et al. |
| 6,375,674 B1 | 4/2002 | Carson |
| 6,389,828 B1 * | 5/2002 | Thomas ....................... 62/186 |
| 6,402,775 B1 | 6/2002 | Bieberich |
| 6,406,427 B1 | 6/2002 | Williams et al. |
| 6,409,745 B1 | 6/2002 | Ducharme et al. |
| 6,416,480 B1 | 7/2002 | Nenov |
| 6,432,124 B1 | 8/2002 | Worthen et al. |
| 6,451,045 B1 | 9/2002 | Walker et al. |
| 6,473,920 B1 | 11/2002 | Augustine et al. |
| 6,487,871 B1 | 12/2002 | Augustine et al. |
| 6,497,720 B1 | 12/2002 | Augustine et al. |
| 6,497,721 B1 | 12/2002 | Ginsburg et al. |
| 6,508,831 B1 | 1/2003 | Kushnir |
| 6,511,502 B1 | 1/2003 | Fletcher |
| 6,516,224 B1 | 2/2003 | Lasersohn et al. |
| 6,519,964 B1 | 2/2003 | Bieberich |
| 6,520,933 B1 | 2/2003 | Evans et al. |
| 6,523,354 B1 | 2/2003 | Tolbert |
| 6,527,798 B1 | 3/2003 | Ginsburg et al. |
| 6,544,282 B1 | 4/2003 | Dae et al. |
| 6,547,811 B1 | 4/2003 | Becker et al. |

| Patent Number | Date | Inventor |
|---|---|---|
| 6,551,347 B1 | 4/2003 | Elkins |
| 6,551,348 B1 | 4/2003 | Blalock et al. |
| 6,551,349 B1 | 4/2003 | Lasheras et al. |
| 6,558,412 B1 | 5/2003 | Dobak, III |
| 6,558,413 B1 | 5/2003 | Augustine et al. |
| 6,576,002 B1 | 6/2003 | Dobak, III |
| 6,581,400 B1 | 6/2003 | Augustine et al. |
| 6,582,398 B1 | 6/2003 | Worthen et al. |
| 6,582,455 B1 | 6/2003 | Dobak, III et al. |
| 6,599,312 B1 | 7/2003 | Dobak, III |
| 6,607,517 B1 | 8/2003 | Dae et al. |
| 6,610,083 B1 | 8/2003 | Keller et al. |
| 6,620,187 B1 | 9/2003 | Carson et al. |
| 6,620,188 B1 | 9/2003 | Ginsburg et al. |
| 6,620,189 B1 | 9/2003 | Machold et al. |
| 6,623,516 B1 | 9/2003 | Saab |
| 6,635,076 B1 | 10/2003 | Ginsburg |
| 6,645,232 B1 | 11/2003 | Carson |
| 6,645,234 B1 | 11/2003 | Evans et al. |
| 6,656,208 B1 | 12/2003 | Grahn et al. |
| 6,656,209 B1 | 12/2003 | Ginsburg |
| 6,692,518 B1 | 2/2004 | Carson |
| 6,800,087 B1 | 10/2004 | Papay et al. |
| 6,887,199 B1 | 5/2005 | Bridger et al. |
| 2001/0021866 A1 | 9/2001 | Dobak, III et al. |
| 2001/0027333 A1 | 10/2001 | Schwartz |
| 2001/0027334 A1 | 10/2001 | White |
| 2001/0039439 A1* | 11/2001 | Elkins et al. .......... 607/104 |
| 2001/0049545 A1 | 12/2001 | Lasersohn et al. |
| 2001/0051801 A1 | 12/2001 | Lehmann et al. |
| 2002/0002394 A1 | 1/2002 | Dobak, III |
| 2002/0004729 A1 | 1/2002 | Zak et al. |
| 2002/0007201 A1 | 1/2002 | Grahn et al. |
| 2002/0029073 A1 | 3/2002 | Schwartz |
| 2002/0032473 A1 | 3/2002 | Kushnir et al. |
| 2002/0091428 A1 | 7/2002 | Larnard et al. |
| 2002/0091431 A1 | 7/2002 | Gunn et al. |
| 2002/0095200 A1 | 7/2002 | Dobak, III et al. |
| 2002/0095201 A1 | 7/2002 | Worthen et al. |
| 2002/0099427 A1 | 7/2002 | Dobak, III |
| 2002/0103520 A1 | 8/2002 | Latham |
| 2002/0116041 A1 | 8/2002 | Daoud |
| 2002/0120317 A1 | 8/2002 | Fletcher |
| 2002/0151946 A1 | 10/2002 | Dobak, III |
| 2002/0183815 A1 | 12/2002 | Nest et al. |
| 2002/0183816 A1 | 12/2002 | Tzeng et al. |
| 2002/0193852 A1 | 12/2002 | Renfro |
| 2002/0193853 A1 | 12/2002 | Worthen et al. |
| 2002/0193854 A1 | 12/2002 | Dobak, III et al. |
| 2002/0193855 A1 | 12/2002 | Dobak, III |
| 2002/0198578 A1 | 12/2002 | Dobak, III |
| 2003/0018375 A1 | 1/2003 | Dobak, III et al. |
| 2003/0023288 A1 | 1/2003 | Magers |
| 2003/0036786 A1 | 2/2003 | Duren et al. |
| 2003/0040782 A1 | 2/2003 | Walker et al. |
| 2003/0040783 A1 | 2/2003 | Salmon |
| 2003/0055472 A1 | 3/2003 | Worthen |
| 2003/0055473 A1 | 3/2003 | Ramsdem et al. |
| 2003/0060863 A1 | 3/2003 | Dobak, III |
| 2003/0060864 A1 | 3/2003 | Whitebrook et al. |
| 2003/0066304 A1 | 4/2003 | Becker et al. |
| 2003/0078638 A1 | 4/2003 | Voorhees et al. |
| 2003/0078639 A1 | 4/2003 | Carson |
| 2003/0078640 A1 | 4/2003 | Carson et al. |
| 2003/0083721 A1 | 5/2003 | Larnard |
| 2003/0088299 A1 | 5/2003 | Magers et al. |
| 2003/0088300 A1 | 5/2003 | Vester |
| 2003/0114903 A1 | 6/2003 | Ellingboe |
| 2003/0135252 A1 | 7/2003 | MacHold et al. |
| 2003/0144714 A1 | 7/2003 | Dobak, III |
| 2003/0150545 A1 | 8/2003 | Szczesuil et al. |
| 2003/0195597 A1 | 10/2003 | Keller et al. |
| 2003/0216799 A1 | 11/2003 | Worthen et al. |
| 2003/0225336 A1 | 12/2003 | Callister et al. |
| 2004/0158303 A1 | 8/2004 | Lennox et al. |

FOREIGN PATENT DOCUMENTS

| | | |
|---|---|---|
| WO | WO 99/08632 | 2/1999 |
| WO | WO 99/44552 A1 | 9/1999 |

* cited by examiner

COOLANT CONTROL FOR RAPID INDUCTION OF MILD HYPOTHERMIA

This application claims priority from U.S. Provisional Application Ser. No. 60/436,433, filed Dec. 23, 2002, the entire content of which is incorporated herein by reference.

TECHNICAL FIELD

The invention relates to medical devices that control the temperature of a patient, and more particularly, to medical devices that cool one or more parts of the body of a patient.

BACKGROUND

Some medical conditions may be treated by hypothermia. In many cases, hypothermic therapy within the first few minutes of the onset of a condition may mean the difference between life and death. In some cases, in which the patient is spared death, prompt hypothermic therapy may make a dramatic difference in the quality of life of the patient.

Stroke is an example of a medical condition that may be treated by prompt administration of hypothermic therapy. Many patients that suffer strokes die as a result of the stroke, and a significant fraction of those who survive suffer some degree of neurological damage. The neurological damage to the patient may be slowed by the application of hypothermic therapy.

SUMMARY

In general, the invention is directed to techniques for controlling the temperature of a coolant delivered to a patient in a hypothermic therapy system. In particular, the invention is directed to techniques for controlling the temperature of a coolant that is delivered to a patient in a gaseous form. In a typical embodiment, one or more cooling garments are placed in contact with the body of a patient, and the cooling garments receive the gaseous coolant. The coolant circulates proximate to the patient and absorbs heat from the patient. As the coolant moves away from the patient, the coolant carries the heat away, thereby cooling the patient.

The degree of cooling is a function of the temperature of the coolant. If the temperature of the coolant is too low, the coolant can harm the patient by causing frostbite or other problems. The invention is directed to systems and methods for controlling the temperature of the coolant.

For a typical system, the coolant originally is introduced in a pressurized liquid form at ambient temperature. When allowed to expand to ambient pressure through a valve, the coolant undergoes a state change from liquid to gaseous form, resulting in a significant drop in temperature. A controller controls the temperature of the coolant delivered to the patient by controlling the flow of coolant through the valve and by combining the expanded coolant with ambient air. The coolant and air are generally mixed in a plenum or chamber. The combination of coolant and air supplied to the patient cools the patient without causing frostbite or other problems.

The controller controls the amount of coolant, air or both as a function of signals from sensors. In many circumstances, the sensors are temperature sensors in the plenum, in the garments, or on the patient. The sensors may also respond to other measures of interest, such as heart rate, blood pressure or blood oxygenation.

In a typical application, an operator such as a rescue worker applies the cooling garments to the patient "in the field," i.e., away from a hospital. The rescue worker brings the coolant to the site in pressurized liquid form at ambient temperature. A very short distance away from the patient, the pressurized coolant is allowed to expand and cool, is mixed with ambient air, and is then applied to the patient. Because the coolant depressurizes and cools proximate to the patient, there is less risk that ambient conditions will unpredictably affect the temperature of the coolant before the coolant can be applied to the patient.

The invention is not limited to application in the field. On the contrary, the invention may be adapted to a hospital setting as well.

In one embodiment, the invention is directed to a device that includes a valve to receive a pressurized coolant at a first temperature and to discharge a depressurized gaseous coolant at a second temperature. The device also includes a plenum to receive the depressurized gaseous coolant and to combine the depressurized gaseous coolant with air at a third temperature, and a garment for placing in contact with a body of a patient to circulate the combined gaseous coolant and air proximate to the body of the patient.

In another embodiment, the invention is directed to a system comprising a valve to receive a pressurized coolant at a first temperature and to discharge a depressurized gaseous coolant at a second temperature, and a plenum to receive the depressurized gaseous coolant and to combine the depressurized gaseous coolant with air at a third temperature. The system also includes a controller to control the valve as a function of a signal from a temperature sensor. The temperature sensor may disposed, for example, in the plenum or in a cooling garment.

In an additional embodiment, the invention presents a method comprising receiving a pressurized coolant at a first temperature, expanding the pressurized coolant to generate a depressurized gaseous coolant at a second temperature, and delivering the depressurized gaseous coolant to a patient. The coolant may be mixed with air before delivery to the patient.

The invention may bring about one or more advantages. The invention offers an efficient cooling system without the need for a bulky refrigeration apparatus to regulate the temperature of the coolant. The supplied coolant may be at ambient temperature, and may be cooled and temperature-regulated proximate to the patient. The temperature of the coolant delivered to the patient can be controlled by regulation of the flow of coolant or by regulation of the ambient air combined with the coolant, or both. Moreover, the temperature of the coolant may be regulated to support different cooling modes.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
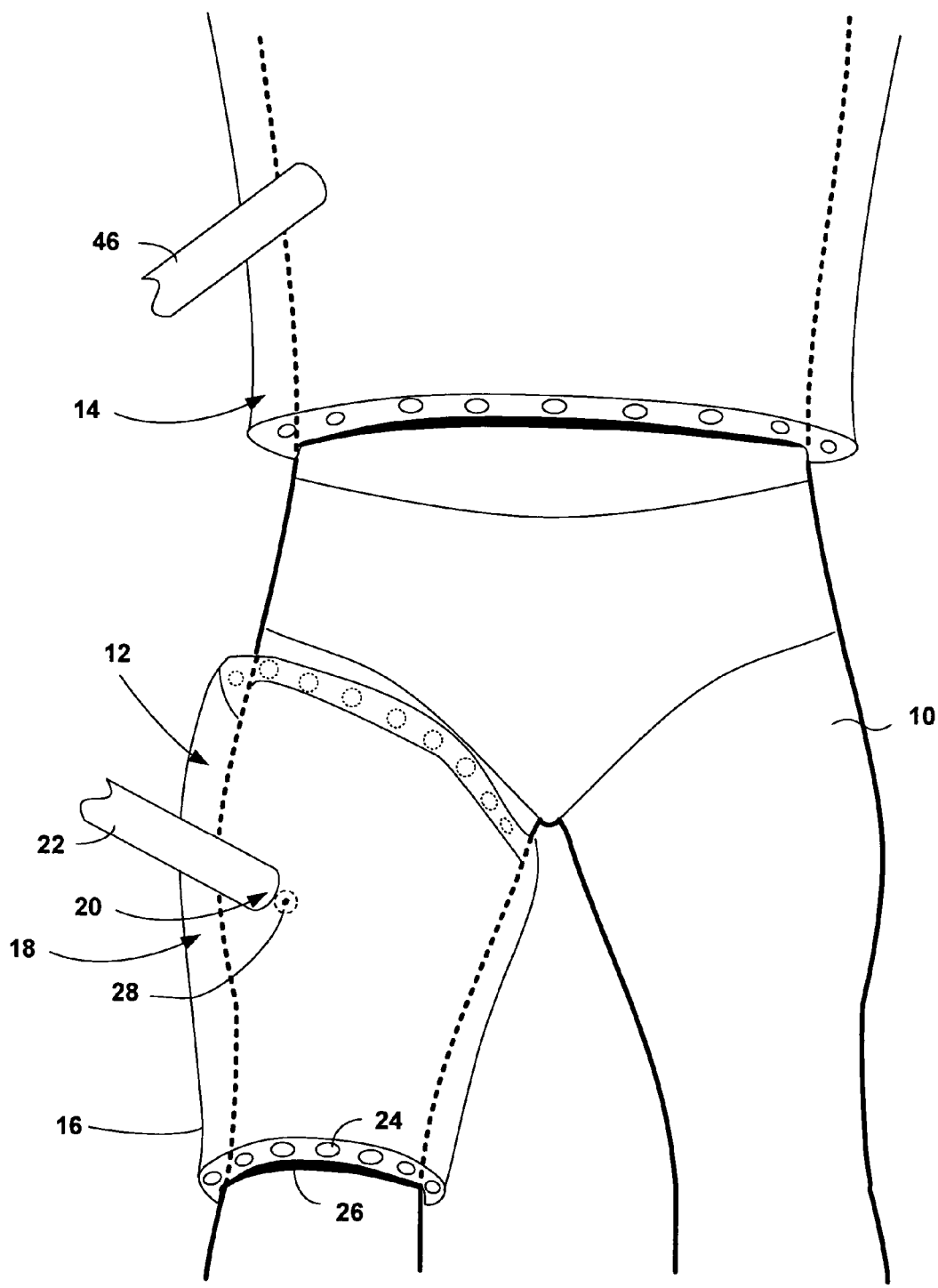
FIG. 1 is a diagram of a patient wearing exemplary cooling garments for which coolant can be controlled, according to an embodiment of the invention.

FIG. 1 is a diagram showing the midsection of a patient 10 receiving cooling therapy with cooling garments. In particular, FIG. 1 shows patient 10 wearing a lower body gear 12 and an upper body gear 14. Although lower body gear 12 will be described in detail, it is assumed for simplicity that lower body gear 12 and upper body gear 14 have similar construction and operate in a similar fashion. The invention is not limited to use with the particular cooling garments shown in FIG. 1, however.

In the embodiment shown in FIG. 1, lower body gear 12 includes a shell 16 that surrounds at least a portion of the body of patient 10, such as an upper thigh. Shell 16 may be constructed of a flexible material that may conform to the shape of the body of patient 10. Shell 16 may further be constructed of an outer material, such as canvas, and an inner material, such as a vinyl liner. Fasteners (not shown), such as a zipper, a hook and loop fastener such as VELCRO, an adhesive, a button, a clip, a strap, a buckle or the like, hold lower body gear 12 and adjust to fit lower body gear 12 on bodies of varying shapes and sizes. When in place, lower body gear 12 defines a space 18 between shell 16 and the body of patient 10. Lower body gear 12 may include a spacer (not shown) that separates at least a portion of lower body gear 12 from the body of patient 10 to maintain space 18.

Lower body gear 12 includes a coolant port 20 that receives a coolant delivery conduit 22. Coolant port 20 brings coolant delivery conduit 22 into fluid communication with garment space 18. The coolant delivered to lower body gear 12 via coolant delivery conduit 22 includes a chilled gas that circulates in space 18. The chilled gas may include a mixture of coolant and ambient air. The chilled gas absorbs heat from the body of patient 10. Supply of the chilled gas via delivery conduit 22 forces the chilled gas in space 18 to exit lower body gear 12 via one or more exit ports 24. A sealing member 26 in contact the body of patient 10 substantially prevents the chilled gas from escaping from lower body gear 12 by a route other than through exit ports 24.

Lower body gear 12 may include one or more temperature sensors 28. Examples of temperature sensors include thermistors, piezo-electric transducers, thermocouples, infrared sensors, and the like. Temperature sensor 28 may respond to the temperature of the chilled gas in space 18, or the temperature of the chilled gas entering space 18 through coolant port 20, or the body temperature of patient 10, or any combination thereof. In one embodiment, a lead (not shown) extends from temperature sensor 28 along coolant delivery conduit 22 to a controller, as will be described below. Lower body gear 12 or upper body gear 14 may also include other sensors (not shown), such as sensors that respond to oxygen saturation levels, blood flow, heart rate, respiration, electrocardiogram (ECG) or the like.

Figure 2:
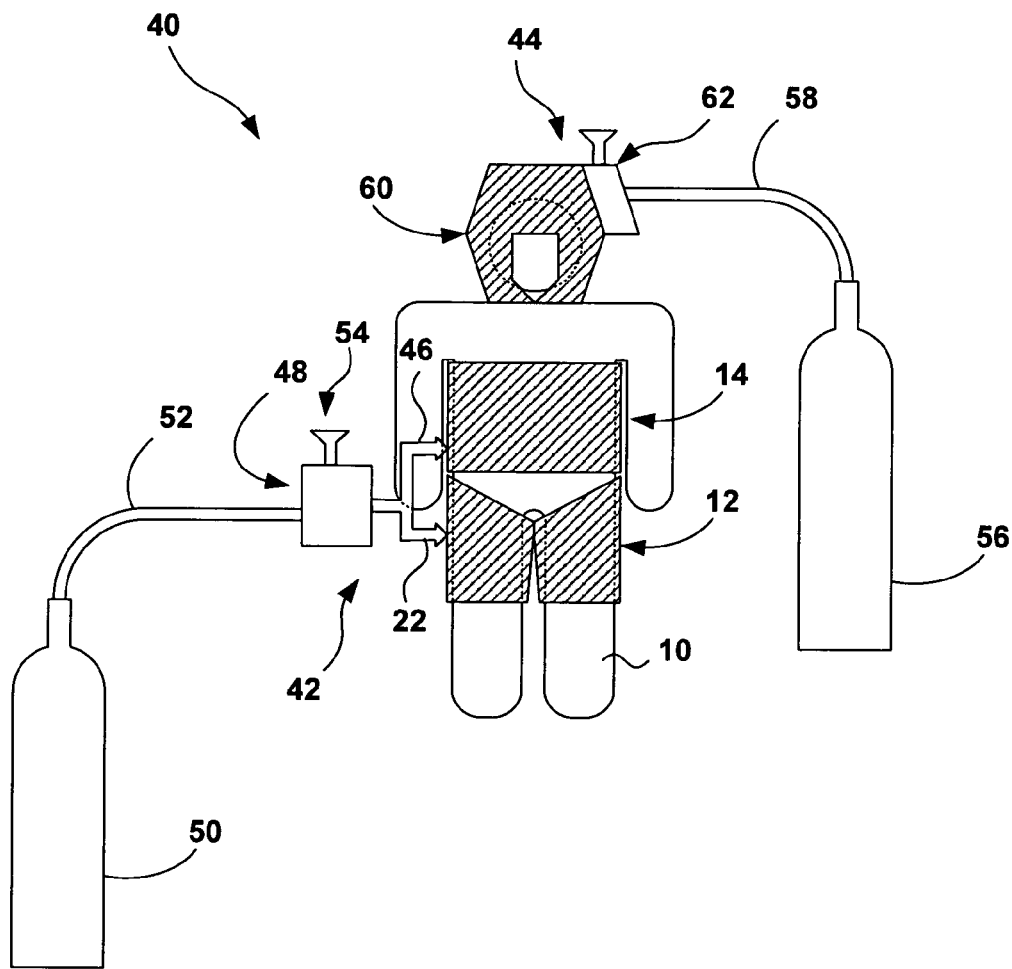
FIG. 2 is a schematic diagram of one or more cooling systems, according to embodiments of the invention.

FIG. 2 is a schematic diagram of a cooling system 40. For purposes of illustration, cooling system 40 in FIG. 2 comprises a body cooling sub-system 42 and a head cooling sub-system 44. Body cooling sub-system 42 includes lower body gear 12 and upper body gear 14. Coolant delivery conduit 22 for lower body gear 12 and coolant delivery conduit 46 for upper body gear 14 receive coolant gas from a single cooling assembly 48, disposed proximate to patient 10. In a typical embodiment, cooling assembly 48 can be disposed within two meters of patient 10. Cooling assembly 48 receives pressurized coolant from a coolant supply 50, which may be remote from patient 10. Coolant from coolant supply 50 arrives in cooling assembly 48 via supply conduit 52.

The coolant in coolant supply 50 may be a pressurized coolant at ambient temperature. In some embodiments of the invention, the coolant in coolant supply 50 is a "pressurized liquid gas," i.e., a pressurized liquid that, at ambient temperature and pressure, exist in a gas state. The coolant may include, for example, carbon dioxide, nitrogen, air, or oxygen. Other coolants are also possible. Although the invention encompasses other coolants as well, including pressurized coolants in gaseous form, the invention will be described in terms of pressurized liquid gas coolant.

The pressurized liquid gas in coolant supply 50 moves under pressure via supply conduit 52 to cooling assembly 48. While moving through supply conduit 52, the coolant is at an ambient temperature. At cooling assembly 48, the coolant expands to ambient pressure. The coolant also undergoes a state change, from liquid to gas. As the coolant expands, the temperature of the coolant drops. In other words, the coolant remains in a liquid form at ambient temperature until the coolant is proximate to patient 10, when the coolant expands and cools. Cooling garments 12 and 14 receive the cooled coolant.

By expanding the coolant in close proximity to patient 10, body cooling sub-system 42 enhances cooling efficiency. Coolant transported in supply conduit 52 is at ambient temperature, so there is less risk that ambient temperature will unpredictably affect the cooling capability of the coolant as the coolant travels to cooling assembly 48. Accordingly, supply conduit 52 need not be insulated to prevent heat transfer. The ambient temperature of the environment may affect the coolant as the coolant is distributed to cooling garments 12 and 14 via coolant delivery conduits 22 and 46, but coolant delivery conduits 22 and 46 are relatively short because cooling assembly 48 is proximate to patient 10. Coolant delivery conduits 22 and 46 may, but need not be, insulated. Additional advantages may result from cooling assembly 48 being proximate to patient 10, as discussed below.

Expansion of the coolant in cooling assembly 48 causes a significant drop in coolant temperature, especially when the coolant undergoes a state change. Pressurized liquid carbon dioxide, for example, may cool to approximately $-78°$ C. ($-108°$ F.) upon expansion to one atmosphere. The expansion of the coolant represents an efficient technique for dropping the temperature of the coolant, but it is possible for the cooled coolant to be cold enough to do harm. In particular, it is possible for the temperature of the coolant to fall so low that application of the cooled coolant gas to patient 10 may cause frostbite.

Accordingly, an intake port 54 receives air at ambient temperature from the environment, and cooling assembly 48 mixes the ambient air with the cooled coolant to produce a coolant-air mixture at a desired temperature. The coolant-air mixture is delivered to the patient via delivery conduits 22 and 46.

Head cooling sub-system 44, like body cooling sub-system 42, includes a coolant supply 56 and a supply conduit 58. A headgear cooling garment 60 circulates cooled gas around the head of patient 10. Head cooling sub-system 44 includes a cooling assembly 62 proximate to patient 10, and in the example shown in FIG. 2, cooling assembly 62 is directly coupled to cooling headgear 60.

The pressurized liquid gas in coolant supply 56 moves under pressure via supply conduit 58 to cooling assembly 62, where the coolant expands to ambient pressure and the temperature of the coolant drops. The coolant may be mixed with ambient air received through an intake port 58, and cooling assembly 62 supplies the coolant-air mixture directly to cooling headgear 60.

As shown in the example of FIG. 2, head cooling sub-system 44 is a sub-system separate from body cooling sub-system 42. The invention encompasses embodiments in which all cooling garments share a single coolant supply or a single cooling assembly.

Figure 3:
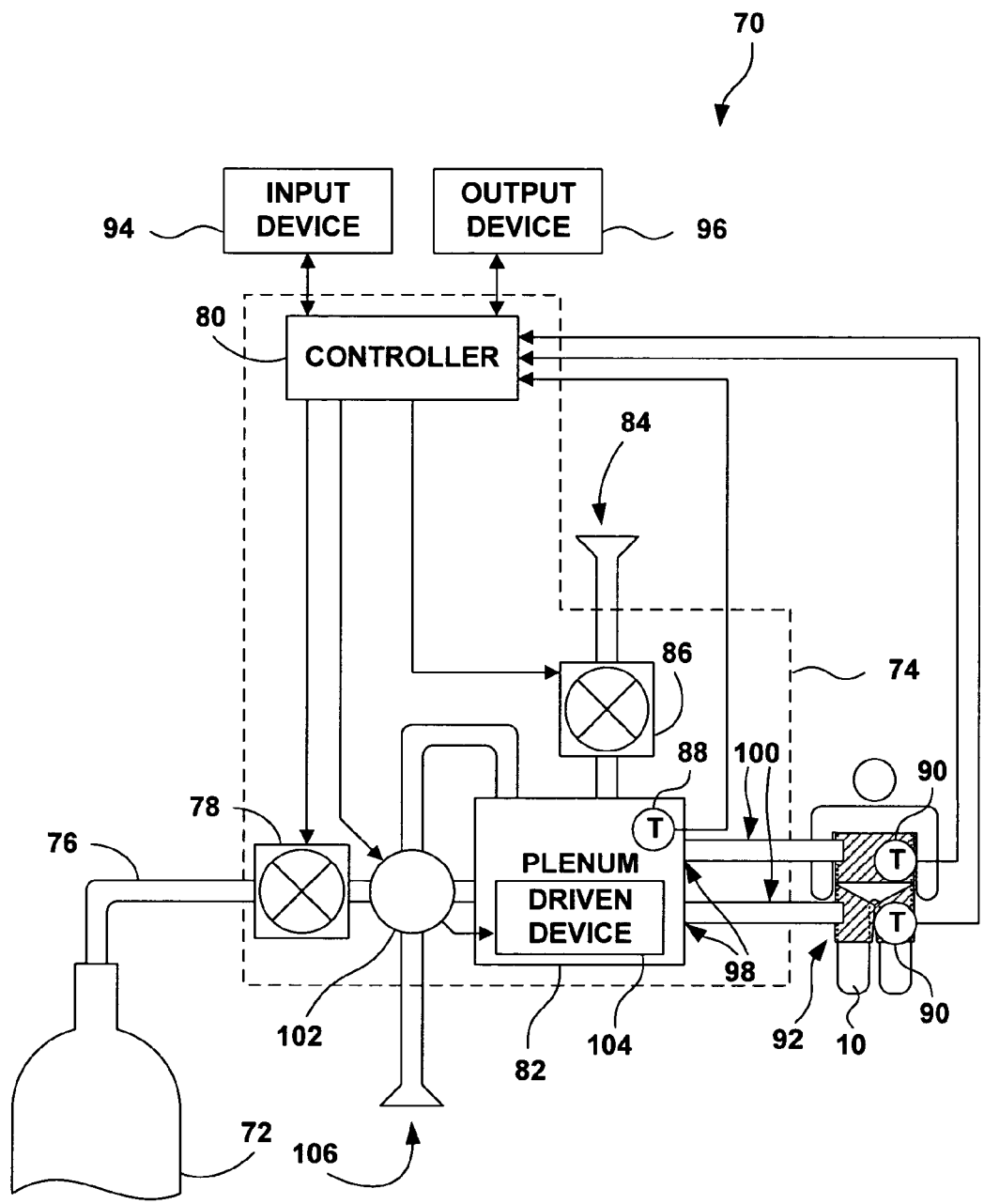
FIG. 3 is a schematic diagram of a cooling system according to an exemplary embodiment of the invention.

FIG. 3 is a schematic diagram of a cooling system 70, which may be adapted to cool patient 10 via body garments 12, 14 or headgear 60. Pressurized coolant from coolant supply 72 is transported to cooling assembly 74 via supply conduit 76. Pressurized coolant is generally at a relatively high temperature, typically ambient temperature.

Coolant expands at valve 78, under the control of controller 80. Valve 78 may be any of several kinds of controllable valves, such as an electronically controlled needle valve, gate valve or ball valve. Valve 78 may be of any size or capacity, and may have cryogenic capabilities.

As the coolant passes through valve 78 and expands, the coolant cools. In the case of a pressurized liquid gas coolant, the coolant also undergoes a state change from a liquid to a gaseous state. The depressurized gaseous coolant may be very cold, and may cause frostbite if applied to patient 10 directly. Accordingly the depressurized gaseous coolant may be directed into a plenum 82, and ambient air may be drawn into plenum 82 through an intake port 84. An intake valve 86, under the control of controller 80, regulates the quantity of ambient air introduced into plenum 82. The ambient air may be drawn in into plenum 82 by movement of gases through plenum 82, creating a pressure gradient according to Bernoulli's principles. The ambient air may also be drawn actively into plenum 82 with an air-moving device such as a fan (not shown). The depressurized gaseous coolant mixes with the ambient air in plenum 82, creating a coolant-air mixture. The temperature of the coolant-air mixture is greater than that of the chilled coolant, and less than that of the ambient air.

Controller 80 monitors the temperature of the coolant-air mixture in plenum 82 via a temperature sensor 88. Controller 80 controls valves 78 and 86 as a function of a signal from plenum temperature sensor 88 to introduce coolant and ambient air into plenum 82 to generate a coolant-air mixture at a desired temperature. In particular, controller 80 controls valve 78 to keep coolant in supply conduit 76 under pressure, and to expand the coolant at a controlled rate. In addition, controller 80 controls valve 86 to control the rate of air flow into plenum 82. By controlling valves 78 and 86, controller 80 controls not only the rate of flow of coolant and air through system 70, but also the temperature of the coolant-air mixture.

In place or in addition to a temperature sensor 88 in plenum 82, system 70 may include temperature sensors 90 in cooling garments 92. Temperature sensors 90 in cooling garments 92 may respond to the temperature of the coolant-air mixture entering or circulating in cooling garments 92, or the body temperature of patient 10, or any combination thereof.

Controller 80 may set a desired temperature for the coolant-air mixture as a function of signals from temperature sensors 90, or control valves 78 and 86, or a combination of both. In this way, controller 80 keeps the coolant-air mixture cool enough to cool patient 10, but not so cold as to cause frostbite.

Controller 80 may also set a desired temperature or control valves 78 and 86 as a function of one or more signals from one or more other sensors (not shown). For example, controller 80 may control valves 78 and 86 as a function of sensors that respond to the vital signs of patient 10 or to the blood oxygenation of patient 10.

Controller 80 may further set a desired temperature or control valves 78 and 86 as a function of instructions from an operator. An operator may interact with controller 80 via one or more input devices 94 and one or more output devices 96. Input device 94 may comprise, for example, a button, keyboard, touch screen voice recognition module or pointing device. Output device 96 may comprise, for example, a display, a touch screen, a speaker, a synthetic speech module or an indicator light. An operator may, for example, direct that cooling assembly 74 apply a specific cooling protocol, such as a "blast cooling mode," that cools patient 10 rapidly. In a blast cooling mode, cooling assembly 74 supplies garments 92 with a coolant-air mixture that would, given prolonged exposure, cause frostbite. Controller 80 limits the time of exposure, however, and after a time interval controls valves 78 and 86 to raise the temperature of the coolant-air mixture to a temperature that will cool patient 10 without causing frostbite.

Controller 80 may support several cooling modes, including a gradual cooling mode, a localized cooling mode, or a rewarming mode in which the amount of coolant delivered to patient 10 is scaled back and the amount of ambient air delivered to patient 10 is increased. An operator may also use input device 94 to direct cooling assembly 74 to discontinue cooling operations.

In the example of FIG. 3, plenum 82 includes multiple exit ports 98 for supplying independent coolant delivery conduits 100 which convey the combined gaseous coolant and air from plenum 82 to cooling garments 92. Although plenum 82 may have a single exit port, plenum 82 may also have multiple exit ports for distribution of combined gaseous coolant and air to various cooling garments.

Optionally, cooling assembly 74 may include a motor 102. In the example of FIG. 3, motor 102 is a gas motor driven by the kinetic energy associated with the expansion of pressurized liquid coolant into a gaseous state. Motor 102 in turn drives another device, such as a motor-driven device 104 in plenum 82. Motor-driven device 104 in plenum 82 may, for example, scrape or flex the sides of plenum 82 to remove ice crystals that can form in plenum 82. Plenum 82 or coolant delivery conduits may include a drip leg or other reservoir (not shown) into which ice crystals and other particulate matter may be deposited. Motor-driven device 104 in plenum 82 may also include a fan to promote mixing of depressurized gaseous coolant with air drawn through air intake 84.

Motor 102 may drive a fan (not shown) to actively draw air into intake port 84. Motor 102 may also serve as an air-moving device, drawing air through an intake port 106 and pumping the air into plenum 82. Controller 80 may control motor 102, and may further control which device or devices will be driven by motor 102.

Cooling assembly 74 may include an air dryer (not shown) that dries air drawn through intakes 84 or 106. An air dryer reduces the formation of ice crystals in plenum 82.

Plenum 82 may be formed of any material, such as metal or plastic. Because plenum 82 may be in close proximity to patient 10, plenum 82 may be made from a soft material, such as rubber or silicone, to reduce discomfort to patient 10 should patient 10 come in contact with plenum 82.

The invention is not limited to the specific embodiments depicted in the figures. For example, a single coolant supply can supply coolant to more than one cooling assembly, or a single cooling assembly may include more than one plenum or more than one valve for expanding the pressurized coolant. A single garment may be associated with a dedicated cooling assembly, or several cooling garments may be associated with a single cooling assembly, or several cooling assemblies may be associated with a single cooling garment. The invention encompasses all of these variations, each of which may be associated with advantages. A single cooling assembly associated with a single cooling garment, for example, may support localized and specialized cooling of regions of the body of patient 10, thereby supporting site-by-site cooling. A system that includes one cooling assembly associated with a several cooling garments may be easily portable. In one embodiment of the invention, the components of system 70 may be modular, e.g., cooling assembly 74 may be coupled to a desired number of cooling garments 92.

Temperature sensors other than those depicted in FIG. 3 may be deployed as well. For example, a temperature sensor may be deployed in the mouth, ear or rectum of patient 10. A temperature sensor may also be disposed to sense the temperature of the ambient air. In addition, cooling system 70 may include sensors other than temperature sensors and sensors other than sensors that respond to conditions of the patient. A variation of cooling system 70 may include, for example, a humidity sensor that responds to the humidity of the ambient air, an ice sensor that responds to the presence of ice in plenum 82, or a flow rate sensor that responds to the flow of coolant to patient 10.

Cooling system 74 may also include a battery or a line power adapter. Cooling system 74 may further include a heater to deliver warmed air to patient 10 via cooling garments 92.

Figure 4:
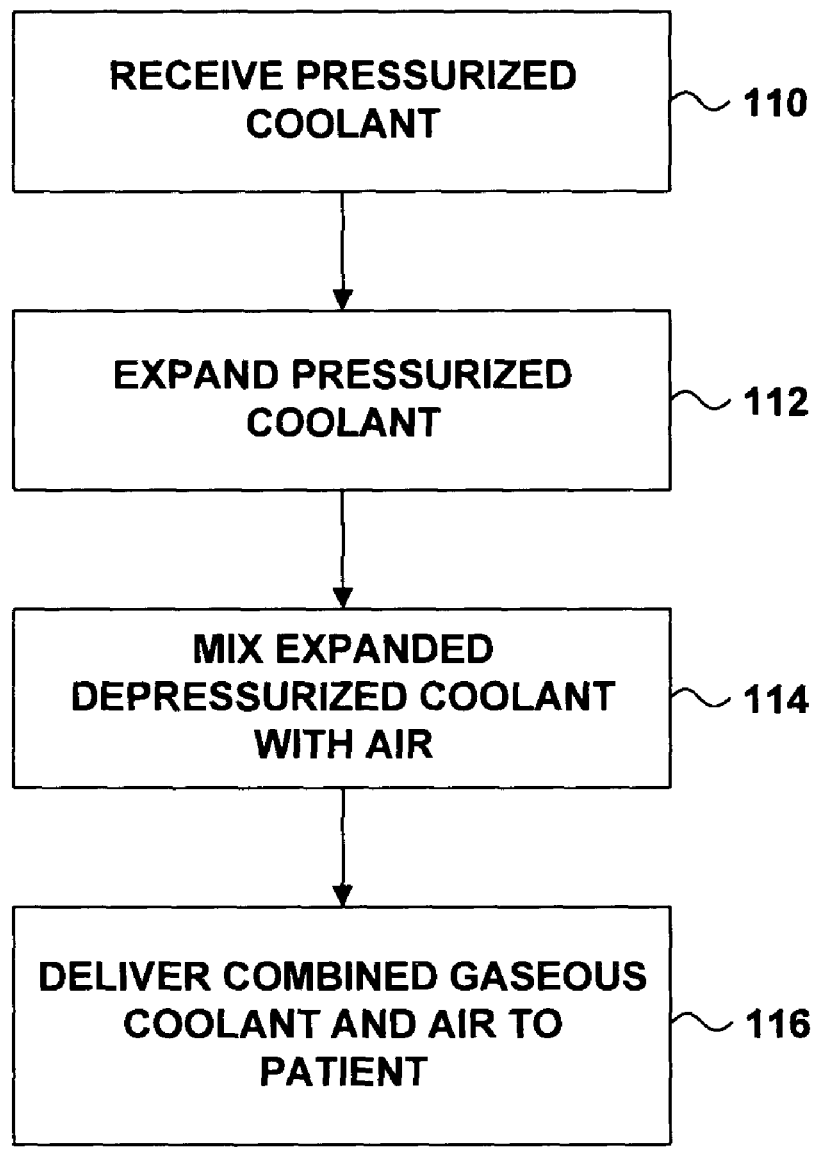
FIG. 4 is a flow diagram illustrating a cooling technique according one embodiment of the invention.

FIG. 4 is a flow diagram illustrating a technique for controlling the temperature of a cooling gas delivered to a patient in a hypothermic therapy system. Cooling assembly 74 receives pressurized coolant from a coolant supply and supply conduit (110). When received, the coolant is typically at a temperature insufficient to cool patient 10, such as ambient temperature. Cooling assembly 74 expands the pressurized coolant through valve 78, under the control of controller 80 (112). If the received coolant is in the form of compressed liquid gas, expansion causes the coolant to undergo a state change, becoming a depressurized coolant in gaseous form. When expanded, the coolant cools.

When expansion causes the coolant to become too cold for application to patient 10, cooling assembly 74 combines the depressurized coolant in gaseous form with ambient air (114). The combination of depressurized gaseous coolant and air results in a gas that can cool patient 10 without causing injury. Air drawn through intake port 84 and intake valve 86, for example, under the control of controller 80, may be mixed with depressurized gaseous coolant in plenum 82. Cooling assembly 74 delivers the depressurized gaseous coolant, combined with the ambient air, to patient 10 (116). A cooling garment may circulate the depressurized gaseous coolant proximate to patient 10, cooling patient 10.

Controller 80 can control the flow of pressurized coolant as a function of a signal from a sensor. For example, controller 80 can monitor a temperature proximate to patient 10 or proximate to plenum 82, and can increase or decrease the amount of coolant expanded as a function of signals from temperature sensors.

The invention may provide one or more advantages. In particular, the invention can be adapted to emergency use in the field. It is unnecessary to bring bulky refrigeration apparatus to the site to of the emergency. The coolant need not arrive at the site in a refrigerated condition. Rather, expansion of the coolant proximate to the patient generates cooled coolant near the site where the cooled coolant will be needed. Although the invention is well-suited for application outside a hospital setting, the invention also may be applied in a hospital setting such as an emergency room or intensive care unit.

Moreover, the temperature of the coolant delivered to the patient can be controlled by regulation of the flow of coolant or by regulation of the ambient air combined with the coolant, or both. Expanded coolant, which by itself might cause frostbite, can be brought to a safer temperature. In addition, the invention supports many cooling modes. The patient may be cooled gradually, rapidly at a moderate pace, or any combination thereof.

These embodiments are illustrative of the practice of the invention. Various modifications may be made without departing from the scope of the claims. For example, the invention may be combined with other apparatus, and need not stand alone. In FIG. 2, for example, a cooling assembly is incorporated with a cooling garment. A cooling assembly may also be incorporated with other rescue devices as well, such as a defibrillator or a monitor.

The invention may support a variety of cooling garments, and is not limited to the garments depicted herein. The cooling garments may be, for example, loose-fitting, or hard-shelled, or directed to other parts of the body of the patient. These and other embodiments are within the scope of the following claims.

The invention claimed is:

1. A device comprising:
    a valve to receive a pressurized coolant at a first temperature and to discharge a depressurized gaseous coolant at a second temperature;
    a plenum to receive the depressurized gaseous coolant and to combine the depressurized gaseous coolant with air at a third temperature;
    an air intake port;
    an air intake valve to control passage of air through the air intake port and into the plenum; and
    a garment for placing in contact with a body of a patient to circulate the combined gaseous coolant and air proximate to the body of the patient.

2. The device of claim 1, in which the coolant comprises at least one of oxygen, nitrogen, air and carbon dioxide.

3. The device of claim 1, in which the pressurized coolant comprises a pressurized liquid gas.

4. The device of claim 1, further comprising a coolant supply to store the pressurized coolant and a supply conduit to transport the pressurized coolant to the valve.

5. The device of claim 1, in which the valve that receives the pressurized coolant is disposed less than two meters from the garment.

6. The device of claim 1, further comprising a coolant delivery conduit to convey the combined gaseous coolant and air from the plenum to the garment.

7. The device of claim 1, further comprising a sensor to sense a temperature in the plenum.

8. The device of claim 1, further comprising a motor, in which the discharge of the depressurized gaseous coolant from the valve drives the motor.

9. The device of claim 1, further comprising an air-moving device to move at least one of the depressurized gaseous coolant and the air.

10. A system comprising:
- a valve to receive a pressurized coolant at a first temperature and to discharge a depressurized gaseous coolant at a second temperature;
- a plenum to receive the depressurized gaseous coolant and to combine the depressurized gaseous coolant with air at a third temperature;
- an air intake port;
- an air intake valve to control passage of air through the air intake port and into the plenum; and
- a controller to control the valve as a function of a signal from a temperature sensor.

11. The system of claim 10, in which the temperature sensor is disposed in the plenum.

12. The system of claim 10, further comprising a garment for placing in contact with a body of a patient to circulate the combined gaseous coolant and air proximate to the body of the patient.

13. The system of claim 12, in which the temperature sensor is disposed in the garment.

14. The system of claim 12, in which the valve is disposed less than two meters from the garment.

15. The system of claim 10, further comprising an input device, in which the controller receives commands from an operator via the input device.

16. The system of claim 10, further comprising a coolant supply to supply the pressurized coolant to the valve.

17. The system of claim 16, further comprising a supply conduit to transport the pressurized coolant from the coolant supply to the valve.

18. The system of claim 10, further comprising a motor, in which the discharge of the depressurized gaseous coolant from the valve drives the motor.

19. The system of claim 10, in which the coolant comprises at least one of oxygen, nitrogen, air and carbon dioxide.

20. The system of claim 10, in which the pressurized coolant comprises a pressurized liquid gas.

21. The system of claim 10, in which the controller controls the air intake valve as a function of a signal from the temperature sensor.

22. The system of claim 10, further comprising a second sensor, in which the controller controls the valve as a function of a signal from the second sensor.

23. The system of claim 22, in which the second sensor comprises at least one of an oxygen saturation sensor, a blood flow sensor, a heart rate sensor, a respiration sensor and an electrocardiogram sensor.

24. A device comprising:
- a valve to receive a pressurized coolant at a first temperature and to discharge a depressurized gaseous coolant at a second temperature;
- a plenum to receive the depressurized gaseous coolant and to combine the depressurized gaseous coolant with air at a third temperature;
- a sensor to sense a temperature in the plenum; and
- a garment for placing in contact with a body of a patient to circulate the combined gaseous coolant and air proximate to the body of the patient.

25. The device of claim 24, in which the valve that receives the pressurized coolant is disposed less than two meters from the garment.

26. The device of claim 24, further comprising a coolant delivery conduit to convey the combined gaseous coolant and air from the plenum to the garment.

27. The device of claim 24, further comprising a motor, in which the discharge of the depressurized gaseous coolant from the valve drives the motor.

28. The device of claim 24, further comprising an air-moving device to move at least one of the depressurized gaseous coolant and the air.

29. A system comprising:
- a valve to receive a pressurized coolant at a first temperature and to discharge a depressurized gaseous coolant at a second temperature;
- a plenum to receive the depressurized gaseous coolant and to combine the depressurized gaseous coolant with air at a third temperature;
- a controller to control the valve as a function of a signal from a temperature sensor disposed in the plenum; and
- a garment for placing in contact with a body of a patient to circulate the combined gaseous coolant and air proximate to the body of the patient.

30. The system of claim 29, in which the valve that receives the pressurized coolant is disposed less than two meters from the garment.

31. A system comprising:
- a valve to receive a pressurized coolant at a first temperature and to discharge a depressurized gaseous coolant at a second temperature;
- a plenum to receive the depressurized gaseous coolant and to combine the depressurized gaseous coolant with air at a third temperature;
- a controller to control the valve as a function of a signal from a temperature sensor disposed in the plenum; and
- a motor, in which the discharge of the depressurized gaseous coolant from the valve drives the motor.

* * * * *